(12) United States Patent
Walti et al.

(10) Patent No.: US 8,801,684 B2
(45) Date of Patent: Aug. 12, 2014

(54) COUPLING PART OF A DRAINAGE TUBE UNIT

(75) Inventors: Martin Walti, Zurich (CH); Fabian Joder, Zurich (CH)

(73) Assignee: Medela Holding AG, Baar (CH)

( * ) Notice: Subject to any disclaimer, the term of this patent is extended or adjusted under 35 U.S.C. 154(b) by 217 days.

(21) Appl. No.: 13/024,628

(22) Filed: Feb. 10, 2011

(65) Prior Publication Data

US 2011/0202022 A1    Aug. 18, 2011

(30) Foreign Application Priority Data

Feb. 16, 2010   (CH) .......................................... 191/10
Nov. 11, 2010   (WO) ................ PCT/CH2010/000283

(51) Int. Cl.
*A61M 1/00*    (2006.01)

(52) U.S. Cl.
USPC ............................ 604/319; 604/313; 604/540

(58) Field of Classification Search
None
See application file for complete search history.

(56) References Cited

U.S. PATENT DOCUMENTS

| | | | |
|---|---|---|---|
| 3,631,654 A | 1/1972 | Riely et al. | |
| 4,031,891 A | 6/1977 | Jess | |
| 4,636,313 A | 1/1987 | Vaillancourt | |
| 4,731,260 A | 3/1988 | Balding et al. | |
| 5,134,996 A | 8/1992 | Bell | |
| 5,224,929 A * | 7/1993 | Remiszewski | 604/30 |
| 5,250,038 A * | 10/1993 | Melker et al. | 604/264 |
| 5,738,656 A | 4/1998 | Wagner | |
| 5,797,907 A | 8/1998 | Clement | |
| 2004/0211468 A1 * | 10/2004 | Horton | 137/511 |

FOREIGN PATENT DOCUMENTS

| | | |
|---|---|---|
| DE | 102006018989 | 10/2007 |
| EP | 2078536 | 7/2009 |
| WO | 2005/035033 | 4/2005 |
| WO | 2005/061025 | 7/2005 |
| WO | 2005/110007 | 11/2005 |
| WO | 2008/141470 | 11/2008 |

OTHER PUBLICATIONS

International Search Report for corresponding Swiss Patent App. No. 1912010 dated Jul. 9, 2010.
International Search Report for International Patent App. No. PCT/CH2010/000283, mailed Mar. 25, 2011.

* cited by examiner

*Primary Examiner* — Melanie Hand
(74) *Attorney, Agent, or Firm* — McDonnell Boehnen Hulbert & Berghoff LLP

(57) ABSTRACT

A coupling part of a drainage tube unit for aspirating body fluids by a suction pump includes a patient-side drainage attachment, a pump-side drainage orifice for connection to a drainage tube, and a drainage channel connecting the drainage attachment and the drainage orifice to each other. The coupling part also includes a pump-side first service orifice for connection to a service tube, a second service orifice ending in the interior of the coupling part, a service channel connecting these first and second service orifices, and a device which separates the service channel from the drainage channel. The device permits delivery of fluid from the service channel into the drainage channel and prevents delivery of particles and liquid from the drainage channel into the service channel. The device is arranged in the coupling part at a location that allows a flow through the drainage channel from the drainage attachment to the drainage orifice without passage through the device.

29 Claims, 10 Drawing Sheets

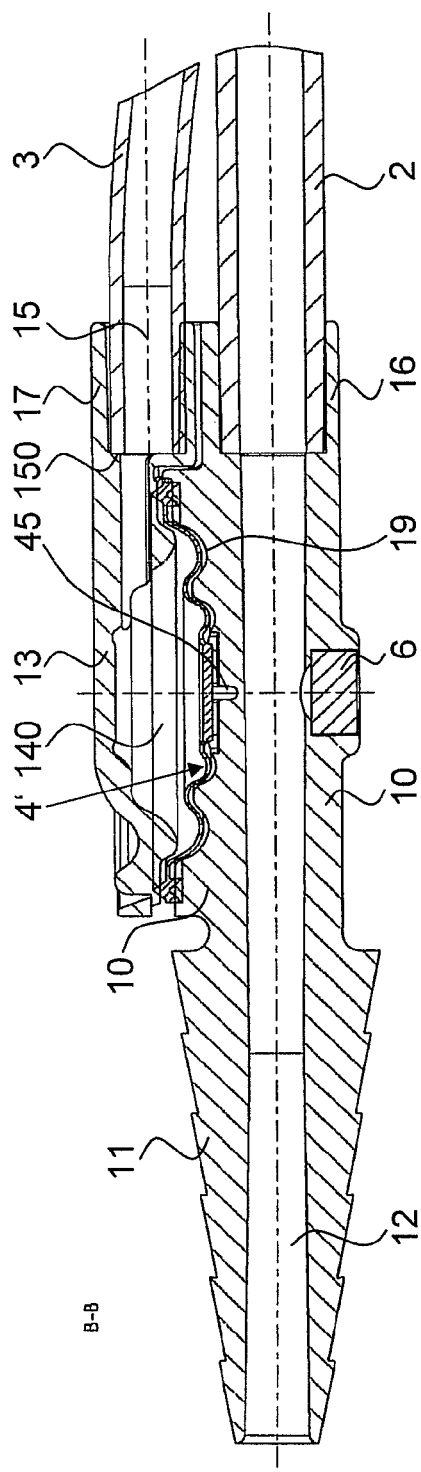
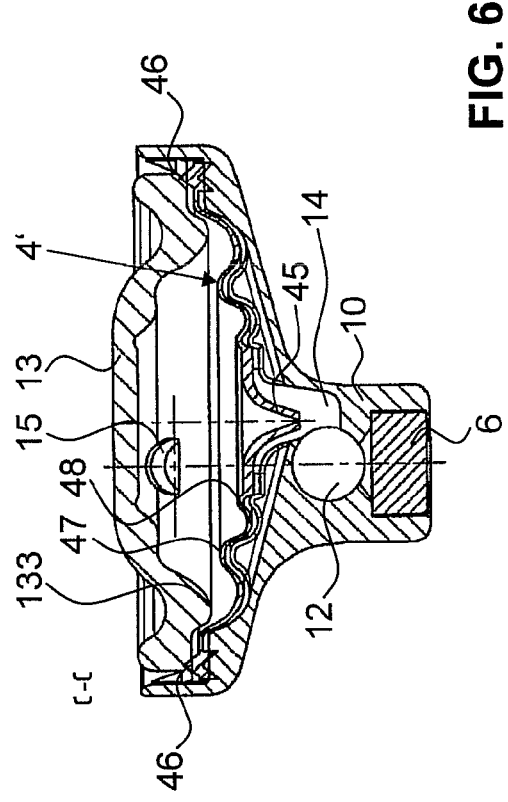
FIG. 5
FIG. 6

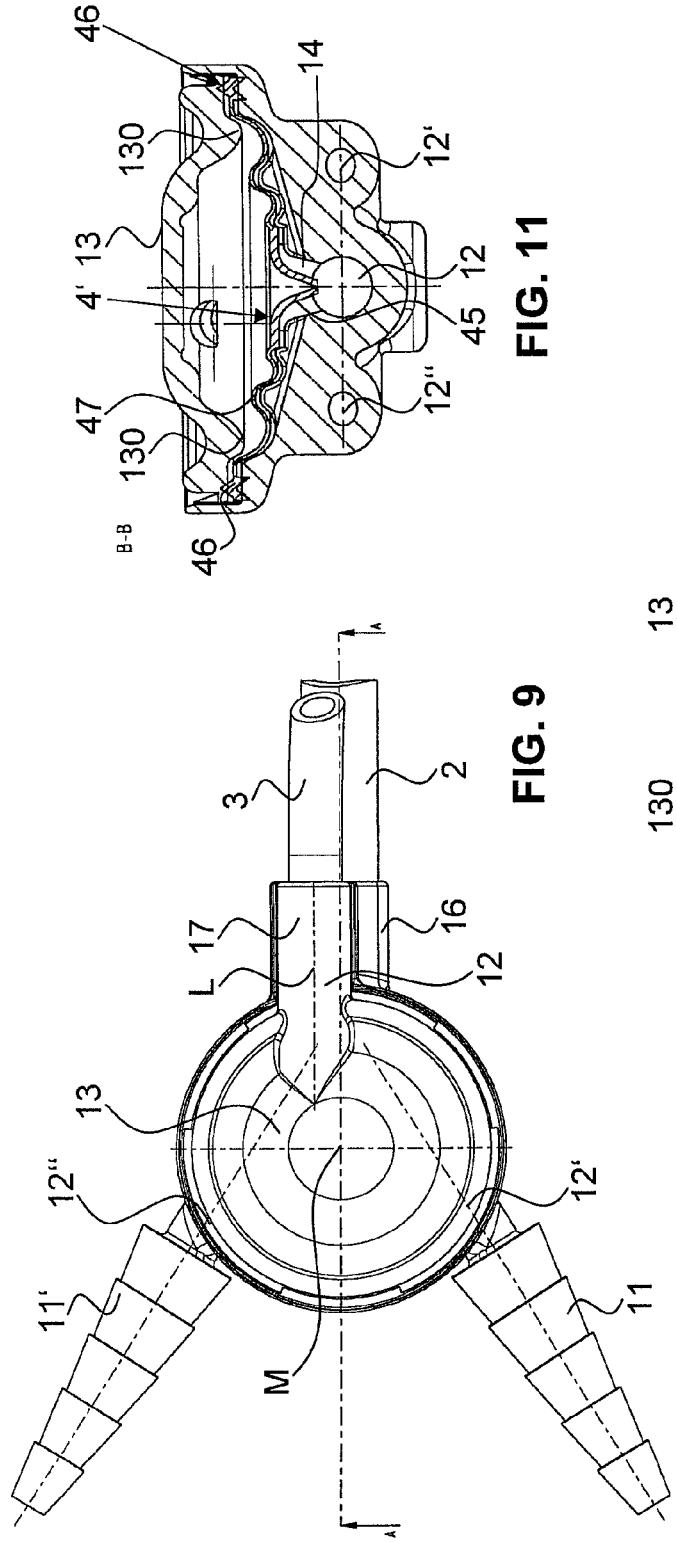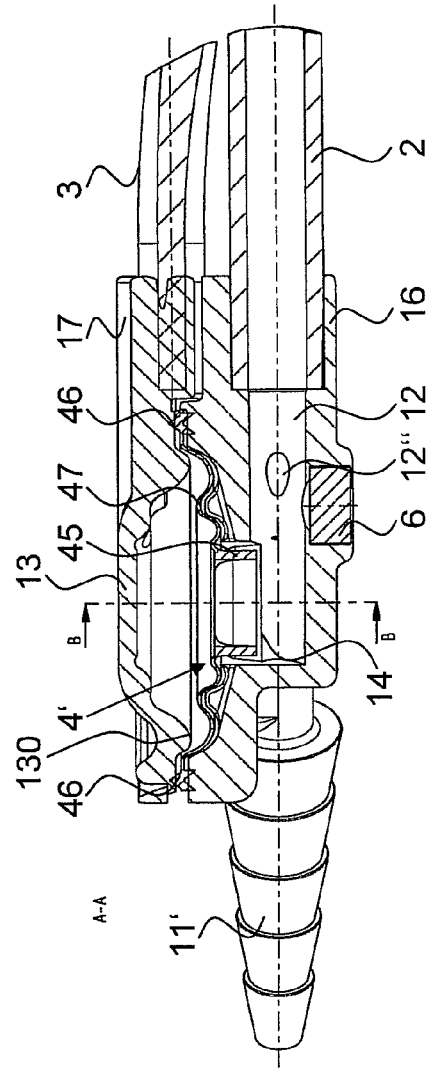

COUPLING PART OF A DRAINAGE TUBE UNIT

CROSS REFERENCE TO RELATED APPLICATIONS

The present application claims priority to Swiss Patent Application No. 00191/10 filed on Feb. 16, 2010 and International Patent Application No. PCT/CH2010/000283 filed on Nov. 11, 2010, the entire contents of which are incorporated here by reference.

TECHNICAL FIELD

The present invention relates to a coupling part of a drainage tube unit, and in particular to a patient-side attachment part.

BACKGROUND

Drainage pump systems are used to aspirate body liquids and fluids in the medical field, for example after surgical interventions, but also in wound drainage, in thorax drainage or in liposuction. These drainage pump systems usually have a suction pump, one or more fluid collection containers, and a drainage tube connection between a patient and fluid collection container. The fluid collection container can be secured releasably on the housing of the drainage pump or can be connected to the pump via a vacuum tube.

With an underpressure being generated in the fluid collection container by means of the suction pump or vacuum pump, the fluid or secretions from a cavity in the patient can be aspirated through the drainage tube into the collection container and collected therein. Filters arranged on the pump-side outlet of the collection container protect the suction pump from possible contamination by the aspirated fluid.

In addition to the drainage line, it is also known to run a service line from the pump to the patient, for example as a measurement line for determining flow differences and pressure differences or for delivering air or gas in order to flush the cavity. Examples of this are disclosed in U.S. Pat. Nos. 5,738,656 and 5,134,996, both of which disclose double-lumen or multi-lumen tubes.

Such measurements of changes in pressure are important aids to physicians and nursing personnel. Changes in pressure during the aspiration provide indications, for example, as to the functionality of the suction pump, the leaktightness of the tube connections, and the healing process.

Moreover, WO 2008/141470 discloses a drainage tube unit for aspirating body fluids by means of a suction pump. The tube unit comprises a pump-side attachment part, a patient-side attachment part, a drainage tube and at least one service tube. The service tube can be used for the abovementioned actions. The tubes are held with a first end in the patient-side attachment part and with a second end in the pump-side attachment part. The ends of the tubes in the patient-side attachment part are held separate from each other in the respective attachment parts and are connected to each other via a connection channel. The drainage tube unit can be produced inexpensively and is easy to use and reliable.

It is also known to use hydrophobic filters in order to avoid contamination of the suction pump. For example, U.S. Pat. No. 4,731,260 discloses a fluid container with a cylindrical filter insert. U.S. Pat. No. 4,636,313 discloses a coupling part of a drainage tube with an integrated bacterial filter.

Devices for removing gases from liquids are also known which use gas-permeable and liquid-impermeable filters. As the liquid flows through these filters, the filters take up the liquid to a certain degree and thereafter do not allow the rest of the liquid to pass through. Examples of these are WO 2005/035033, U.S. Pat. Nos. 3,631,654 and 4,031,891.

SUMMARY

It is an object of the invention to make available a drainage tube unit which ensures that the service line cannot become blocked by aspirated secretions.

The coupling part, according to the invention, of a drainage tube unit for aspirating body fluids or secretions by means of a suction pump includes a patient-side drainage attachment, a pump-side drainage orifice for connection to a drainage tube, and a drainage channel connecting the drainage attachment and the drainage orifice to each other, at least one pump-side first service orifice for connection to a service tube, a second service orifice ending in the interior of the coupling part, a service channel connecting these first and second service orifices, and a device which separates the service channel from the drainage channel. The device permits delivery of fluid from the service channel into the drainage channel and prevents delivery of particles and liquid from the drainage channel into the service channel. The device is arranged in the coupling part at a location that allows a flow through the drainage channel from the drainage attachment to the drainage orifice without passage through the device.

Here, "passage through" is understood as meaning that the fluid does not flow through the separating medium or the separating mechanism of the device. If the device has an area that has no separating function, the fluid can pass through the device in this area. This area can be, for example, a continuous hollow space, as is present in the third and fourth illustrative embodiments described hereinbelow.

The device in the coupling part allows an air exchange to take place between the service channel and the drainage channel. However, the device prevents body fluids and aspirated tissue fragments from being able to pass into the service line. Pressure measurements and flushing procedures with air or gas can thus be carried out unimpeded at any time by means of the service channel.

The coupling part is preferably a patient-side attachment part or a patient-side end plug of a drainage tube unit.

The device can be a one-way valve, in particular a nonreturn valve, a filter, or a combination of the two. The filter is permeable to air but impermeable to liquid. The filter is preferably not only hydrophobic but also oleophobic.

The device is preferably, but not necessarily, designed as a membrane. In a preferred embodiment, the membrane is made from a material that is permeable to air and impermeable to liquid. In this way, a pressure measurement is possible via the service line, without aspirated liquid or aspirated particles being able to pass from the drainage channel into the service channel. The membrane can be completely closed. However, the membrane can also have a nonreturn valve, for example by being designed as a duckbill valve, with the duckbill oriented in the direction of the drainage channel. If, in addition to the material mentioned above, the membrane has this valve, a liquid can also be conveyed through the service line into the drainage channel, nevertheless avoiding liquid being flushed in the opposite direction into the service channel.

It is also possible that the device includes a nonreturn valve made from a material that is impermeable to gas and impermeable to liquid. Here too, the nonreturn valve can be designed in the form of a membrane, particularly in the form of the above-described plate-shaped main body with a preferably centrally arranged duckbill valve.

In preferred embodiments, the membrane has a round, oval or elliptic basic shape, and is preferably in one piece. In a preferred embodiment, the membrane has a one-piece, plate-shaped main body. If present, the nonreturn valve is preferably formed integrally on the main body. The nonreturn valve is in this case preferably arranged in the center of the membrane.

The membrane preferably has, in its peripheral area, at least one circumferential and closed sealing lip. The latter provides a seal against a membrane seat and permits a valve function.

The membrane preferably forms a membrane surface that runs approximately parallel to a longitudinal axis of the drainage channel. The membrane is preferably arranged asymmetrically with respect to a longitudinal center axis of the drainage channel. This has the advantage that the device takes up less space.

The device preferably has a connection channel for connecting the second service orifice to the drainage channel, wherein the device is arranged in the area of this connection channel. This is particularly advantageous when the service channel and the drainage channel are approximately or exactly parallel to each other.

The cross sections of the service channel and, if present, of the connection channel are preferably both smaller than that of the drainage channel.

The membrane, or a differently designed device, is easy to fit if the coupling part has a main body with a seat for receiving the membrane or the device and has a lid with which the main body is closed off in a leaktight manner from the outside in the area of the seat. Production is simplified if the service channel is arranged in the lid.

In a preferred embodiment, an injection and/or withdrawal opening, preferably a channel, is additionally present which connects an outer face of the coupling part to the drainage channel. A fluid can be injected, or a fluid withdrawn, via this opening.

In a first embodiment, the coupling part has exactly one drainage channel and exactly one service channel. In another embodiment, two drainage channels and a single service channel are present, wherein the service channel is connected to both drainage channels, and wherein the device has a single membrane, which separates both drainage channels from the service line.

Instead of the approximately plane or plate-shaped membrane, the device can also have a tubular shape. The device is then preferably coaxial with respect to the drainage channel. In a preferred embodiment, a tubular device of this kind has a support body and a filter element that performs a filter function, wherein the filter element is arranged on and/or in the support body.

The tubular device is preferably arranged in the drainage channel, such that the device also protects the connection channel. In a preferred embodiment, the connection channel has a first end, which opens into the drainage channel, and the filter closes the first end.

In order to optimize a pressure measurement, a free space is formed between an outer periphery of the filter and an inner wall of the drainage channel. The free space can be annular in cross section. However, the free space is preferably formed as a chamber.

The filter is preferably designed as an insert element, and can preferably be pushed into position, ready for use in the inside of the coupling part, by way of an end of the drainage channel towards the suction pump. The filter is preferably compressed in position, such that the compression packing between the filter and the inner wall of the coupling part ensures that no secretion liquid can pass into the service channel.

The filter has a filter material which performs the filter function and which is hydrophobic and preferably also oleophobic. The filter can be composed entirely of this filter material performing the filter function. The filter is then preferably designed in one piece and/or self-supporting.

In a preferred embodiment, however, the filter has a support body and a filter element that performs the filter function. The filter element is then arranged on and/or in the support body. The filter element is preferably designed as a membrane. The support body preferably has a hollow cylindrical shape and has at least at one end, preferably at both ends, a radially outwardly protruding flange. The support body preferably has webs or reinforcing ribs extending in the longitudinal direction. The support body can be produced easily and to precise size, e.g. from plastic by injection moulding. Moreover, the filter element can be easily secured thereon. For example, the filter element can be arranged inside the support body or is wound around the support body. The filter element can also be injected onto the inner face or outer face of the support body. If the filter element is applied to the inner face of the support body, the stiffness of the filter element is thus increased.

In a variant of the invention, the drainage channel is rectilinear along its entire length. The drainage channel preferably has a step, which serves as an abutment surface for the filter. In this case, only a single drainage channel is preferably present.

In this and in other variants of the invention, the filter has a through-channel and is arranged in the coupling part in such a way that body fluid flows through the through-channel during the aspiration.

In other variants of the invention, the filter is arranged in the coupling part at a location through which body fluid does not flow during the aspiration. This embodiment is also suitable in particular for coupling parts that have two or more patient-side drainage attachments and thus serve for bifurcation of the drainage line.

The filter does not necessarily have to be arranged in the drainage channel, and instead can sit at another suitable location as long as it separates the drainage channel from the service channel, i.e. prevents fluid from the drainage channel passing into the service channel without flowing through the filter.

The coupling part is preferably formed by a patient-side attachment part as disclosed in WO 2008/141470, being provided according to the invention with a device described above. However, it is also possible according to the invention to provide differently configured coupling parts with a filter.

Other embodiments are set forth in the dependent claims.

BRIEF DESCRIPTION OF THE FIGURES

Preferred embodiments of the invention are described below with reference to the drawings, which serve only for explanatory purposes and are not to be interpreted as limiting the invention. In the drawings:

FIG. 5 shows a longitudinal section through the coupling part along B-B according to FIG. 3;

FIG. 6 shows a cross section through the coupling part along C-C according to FIG. 4;

FIG. 9 shows the coupling part according to FIG. 7 in a view from below;

FIG. 10 shows a longitudinal section through the coupling part along A-A according to FIG. 9;

FIG. 11 shows a longitudinal section through the coupling part along B-B according to FIG. 10;

DETAILED DESCRIPTION

Figure 1:
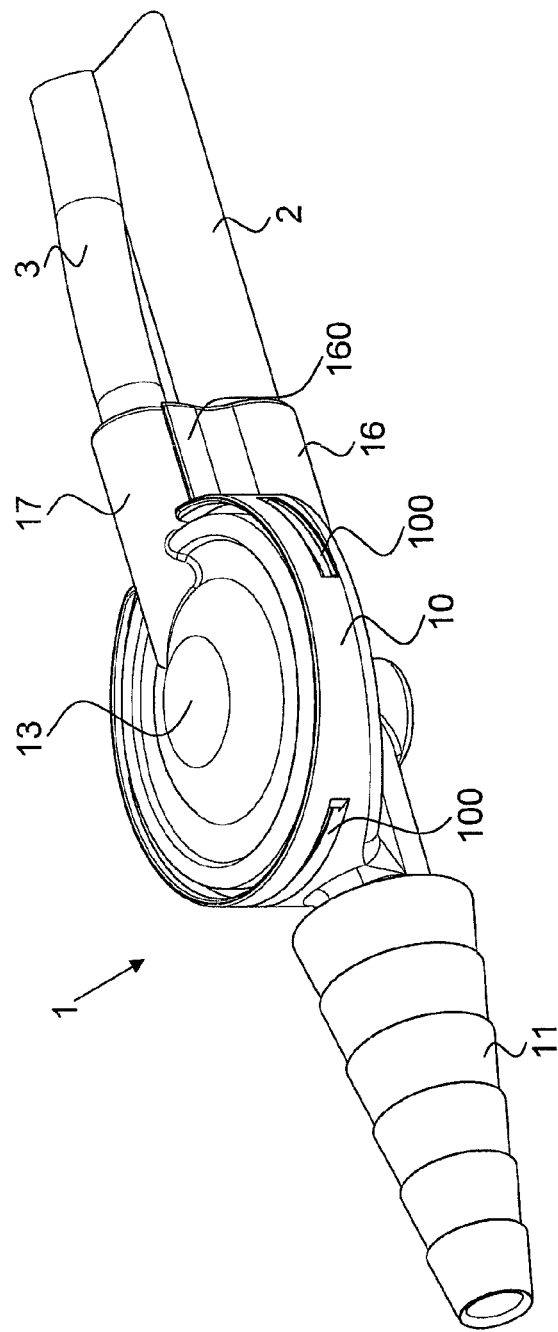
FIG. 1 shows a perspective view of a coupling part according to the invention, with a service tube and a drainage tube attached in a first embodiment, seen from above.

FIG. 1 shows a first embodiment of the coupling part 1 according to the invention, with tubes 2 and 3 arranged therein.

The coupling part has a main body 10 and, arranged thereon, a patient-side drainage attachment 11. The coupling part 1 is preferably made of plastic and by means of injection moulding. In the preferred illustrative embodiment shown here, the main body 10 and the drainage attachment 11 are formed together in one piece.

The main body 10 has, at an end directed away from the patient, a first orifice 16 for receiving the patient-side end of the drainage tube 2. Above this first orifice 16, there is preferably a receiver 160 which is in the shape of a partial tube and is open at the top.

The main body 10 is closed with a closure lid 13. The closure lid 13 is also preferably made of plastic by injection molding. The lid 13 can preferably be connected to the main body 10 by a snap-fit closure. Preferably, once a connection has been established, the connection cannot be undone without breaking. For this purpose, the main body 10 has windows 100 which are distributed about the circumference and in which radially protruding lugs of the lid 13 engage.

In the closure lid 13, there is a second orifice 17 for receiving the patient-side end of the service tube 3. The second orifice 17 is tubular and can click with a form fit into the partially tubular receiver 160 of the main body 10.

The first and second orifices 16, 17 preferably extend parallel to each other, such that the two tubes 2, 3 are guided away in parallel but with a slight space between them.

The service tube 3 preferably serves to measure pressure in the area of the drainage attachment 11. Alternatively or in addition, the service tube 3 can also be used for flushing with a gaseous or liquid fluid, in particular with air. The diameter of the service tube 3 is preferably smaller than the diameter of the drainage tube 2. Both tubes 2, 3 are preferably designed with one lumen and they extend separately from each other at least in the area of the coupling part 1. Both tubes 2, 3 are preferably made of silicone or PVC. The tubes 2, 3 are plugged into the orifices 16, 17 and thus held therein. The tubes 2, 3 are preferably adhesively bonded or welded to the coupling part. Other sealing types of fixing are also possible. For example, in another embodiment, the tubes 2, 3 can also be plugged onto the orifices 16, 17.

Figure 3:
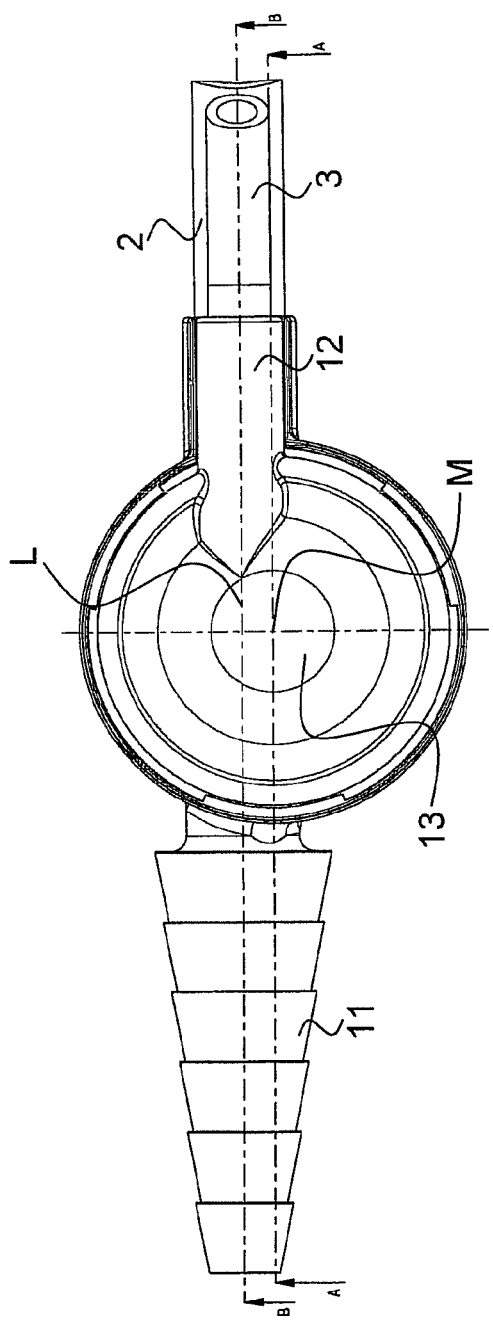
FIG. 3 shows the coupling part according to FIG. 1 in a view from below.

At the opposite end, the main body 10 merges into the patient-side drainage attachment 11. The drainage attachment 11 is preferably conical and stepped, narrowing towards its free, open end. In cross section, the drainage attachment 11 has a Christmas tree shape. The drainage attachment 11 in this example is axially aligned with the pump-side orifice 16 for the drainage tube 2. A drainage channel 12, shown in FIG. 3, which is here depicted as being rectilinear along its entire length, extends between the orifice 16 and the patient-side free end of the drainage attachment 11.

The diameter of the pump-side orifice 17 for the service tube 3 is smaller than that of the pump-side orifice 16 for the drainage tube 2. The second orifice 17 is offset with respect to the first orifice 16 in the main body and leads into a service channel 15 that extends rectilinearly and parallel to the drainage channel 12. The service channel 15 in the interior of the main body 10 preferably narrows and thus forms a step 150 as shown in FIG. 5. The step 150 serves as an abutment for the patient-side end of the service tube 3. The drainage channel 12 and the service channel 15 can be seen, for example, in FIG. 5.

Between the end near the patient and the end directed away from the patient, the main body 10 in this embodiment has a flat round area. The lid 13 is likewise substantially flat and round, which can be seen clearly in FIG. 3. The round area and the lid 13 form a common chamber 140, which can be clearly seen in FIGS. 4 and 5. The chamber 140 connects the service channel 15 to the drainage channel 12, and is described in more detail below.

Figure 4:
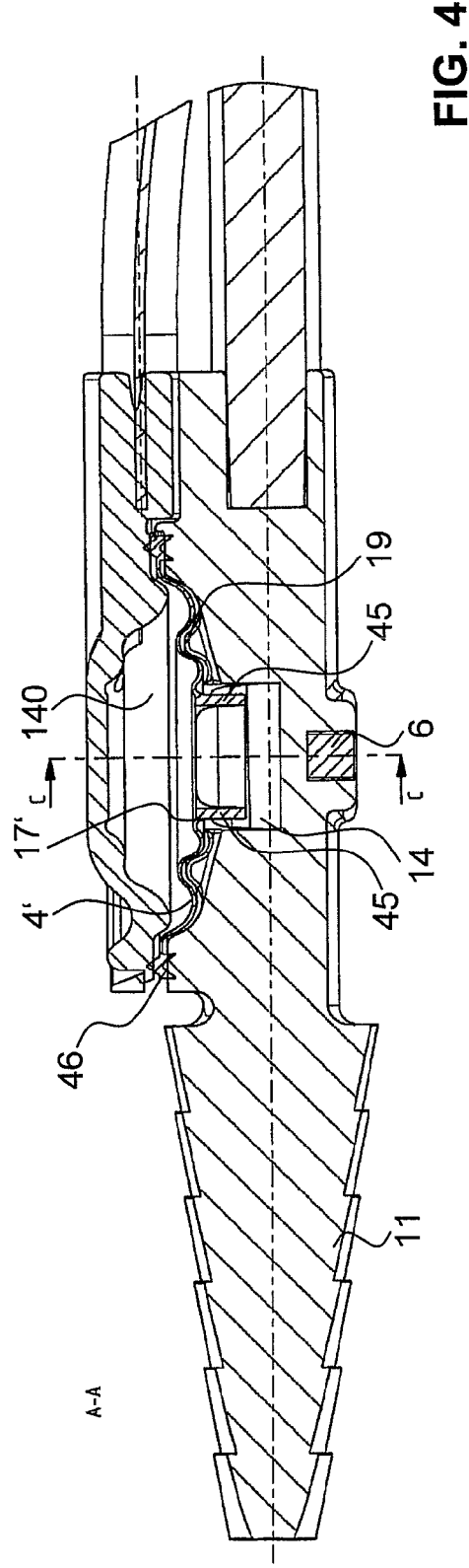
FIG. 4 shows a longitudinal section through the coupling part along A-A according to FIG. 3.
Figure 7:
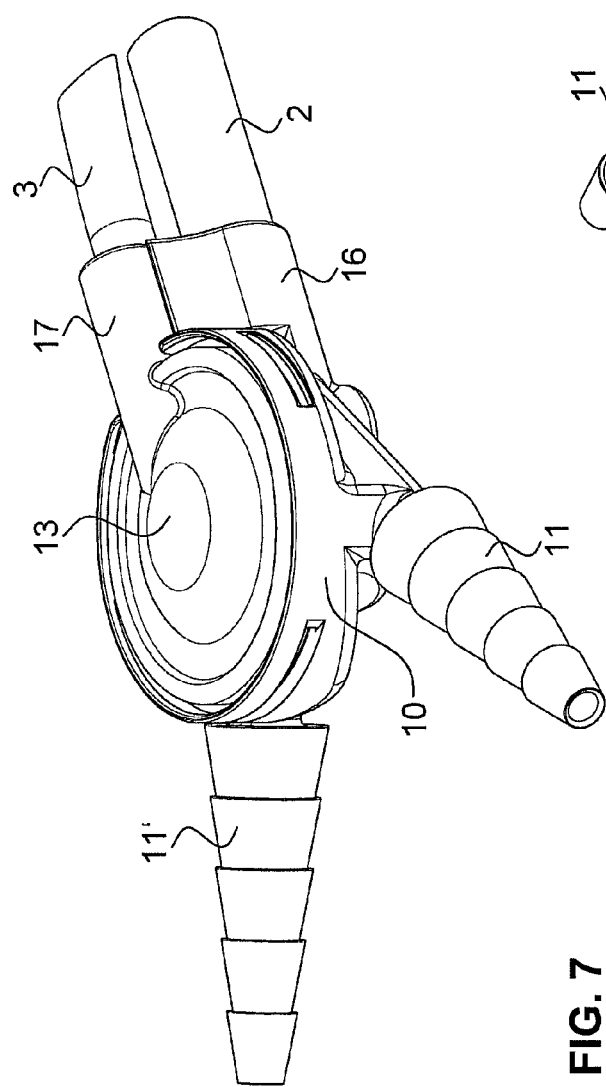
FIG. 7 shows a perspective view of a coupling part according to the invention, with a service tube and a drainage attached tube in a second embodiment, seen from above.
Figure 8:
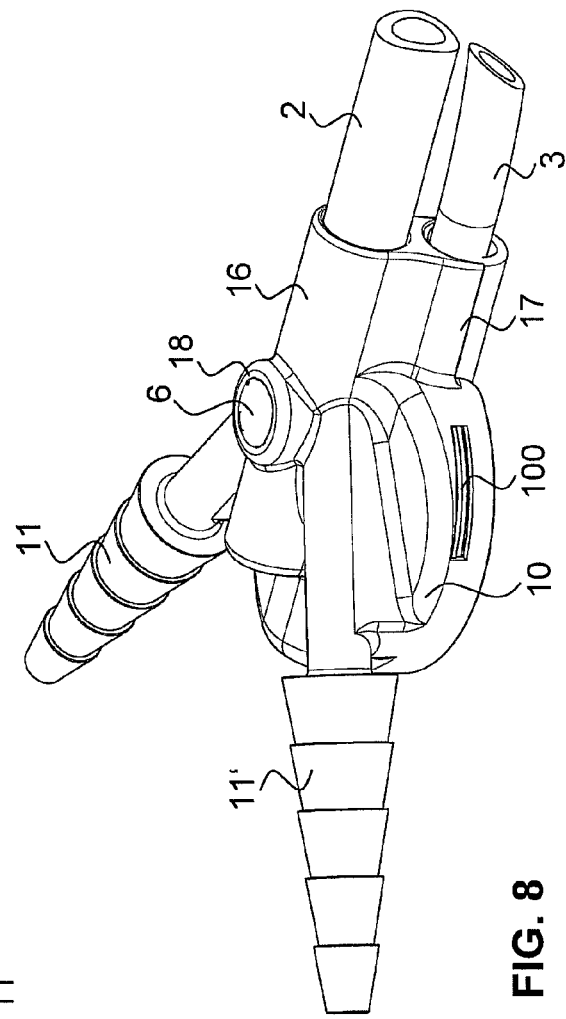
FIG. 8 shows the coupling part according to FIG. 7, with the underside being visible here.

As can be seen from FIGS. 4 and 5, the service channel 15 in the lid 13 ends in the chamber 140, which merges into a connection channel 14. A second orifice of the service channel 15 is designated by reference number 17' in the figures. The connection channel 14 is preferably perpendicular to the service channel 15 and opens out in the drainage channel 12. The connection channel 14 preferably opens out at right angles to the longitudinal axis of the drainage channel 12, and is preferably rectilinear. However, the connection channel 14 can also be at an angle other than 90° with respect to the service channel 15 and/or drainage channel 12 and/or can be curved.

The part of the chamber 140 on the main body side is designed as a membrane seat 19. The membrane seat 19 has a circular raised edge in the peripheral area of the main body 10. This is followed, in the direction toward the center, by a circular depression with a renewed raised rib. The rib is likewise circular. The connection channel 14 begins at the center M of the inner depression, which also preferably corresponds to the center M of the round area of the main body 10. The connection channel 14 preferably extends at right angles to the drainage channel 12. A second end of the connection channel 14 opens into the drainage channel 12, and a first end preferably has a rectangular cross section.

The inner surface of the lid 13 is also correspondingly curved. the inner surface of the lid has in particular a circumferential and closed rib 133, protruding in toward the membrane seat, and an outer plane circumferential surface in the radial direction from the rib 133.

A membrane 4' is arranged in the chamber 140. The membrane 4' is preferably made from an air-permeable but liquid-impermeable material. However, the membrane 4' can also be made from a material that is impermeable to air and liquid. Examples of the materials are elastomers, in particular silicone or TPE (thermoplastic elastomers).

The membrane 4' has a round main contour and, matching the membrane seat 19, is provided with circumferential and completely closed rings 47, 48. The membrane has, in its peripheral area, at least one sealing lip, in this case two concentric sealing lips 46. At least one of the sealing lips has a relatively sharp edge. These sealing lips 46 are supported on the planar peripheral area of the membrane seat 19 and form a leaktight connection together with the radially inwardly succeeding rib 133 of the lid 13. Toward the top, in the direction of the lid 13, a protruding and pointed sealing rib is likewise preferably present in this area.

At its center, the membrane 4' preferably has a duckbill valve 45. The duckbill valve 45 is preferably produced in one piece with the rest of the membrane 4'. The duckbill valve 45 protrudes into the connection channel 14 and thus opens an inlet from the service channel 15 to the drainage channel 12 but closes the opposite direction.

Figure 2:
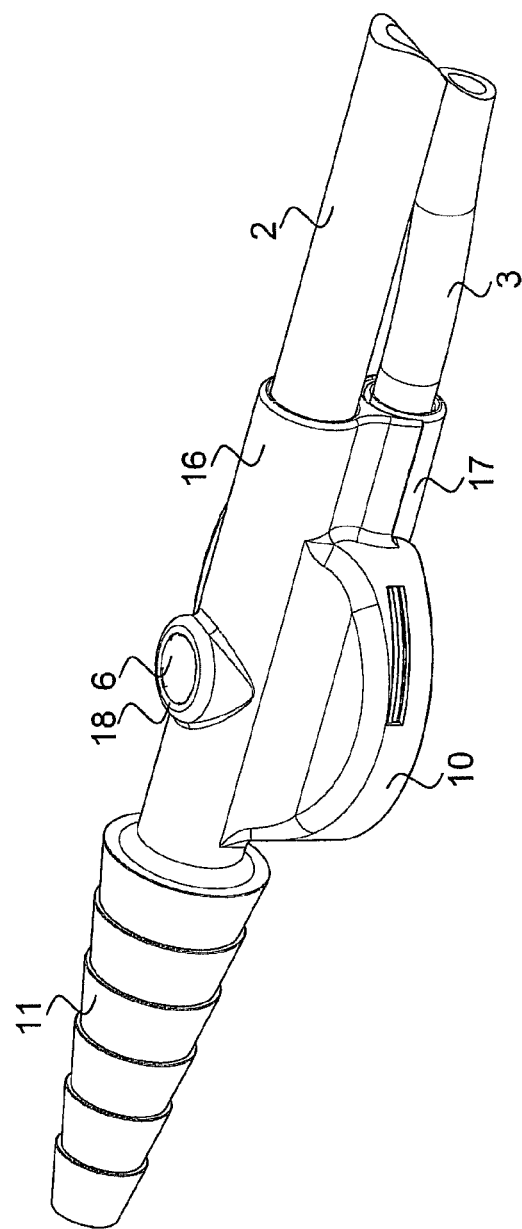
FIG. 2 shows the coupling part according to FIG. 1, with the underside being visible.

As can be seen from FIG. 2, an opening 18 is present on a side of the main body 10 opposite the lid 13. The opening 18 serves as an injection and/or withdrawal opening and, during correct use of the coupling part, allows a liquid or a gas to be injected into the drainage channel 12 and/or to be withdrawn. When not in use, this injection and/or withdrawal opening 18 or the channel is preferably closed in a leaktight manner with a stopper 6. This can be seen clearly in FIGS. 4 to 6.

FIGS. 7 to 11 show a second embodiment of the coupling part 1 according to the invention. Identical parts are provided with the same reference signs. Here too, the main body 10 and the lid 13 closing the plate-shaped area of the main body 10 are present. Lid 13 and main body 10 again form the chamber 140 in which the membrane 4' is arranged. The chamber 140, in particular the membrane seat 19, and the membrane 4' itself are preferably configured in the same way as in the first illustrative embodiment described above. Moreover, in this embodiment, there is also preferably an injection and/or withdrawal opening 18 that can be closed with a stopper 6.

In this embodiment, however, the main body 10 has three ends, such that its connectors form a Y-shape. A first, pump-side end once again has two mutually spaced apart orifices 16, 17 for the drainage tube 2 and the service tube 3. However, there are also two patient-side ends, which are preferably designed identically. At each end there is a patient-side drainage attachment 11, 11'. Both are preferably of the same length, and have the same or smaller cross section as that of the drainage channel 12. The pump-side, single-lumen drainage channel 12 thus divides within the main body 10 into two preferably identical drainage channel branches 12', 12". They preferably divide, in the aspiration direction, upstream of the orifice 17' of the service channel 14 into the drainage channel 12. That is to say, the drainage channel 12 in the main body 10 has a branch that continues beyond the bifurcation of the drainage channel branches 12', 12" and that preferably forms the patient-side rectilinear extension of the drainage channel 12. The extension is preferably long enough to ensure that the nonreturn valve 45 is located completely in the area of the extension.

Figure 12:
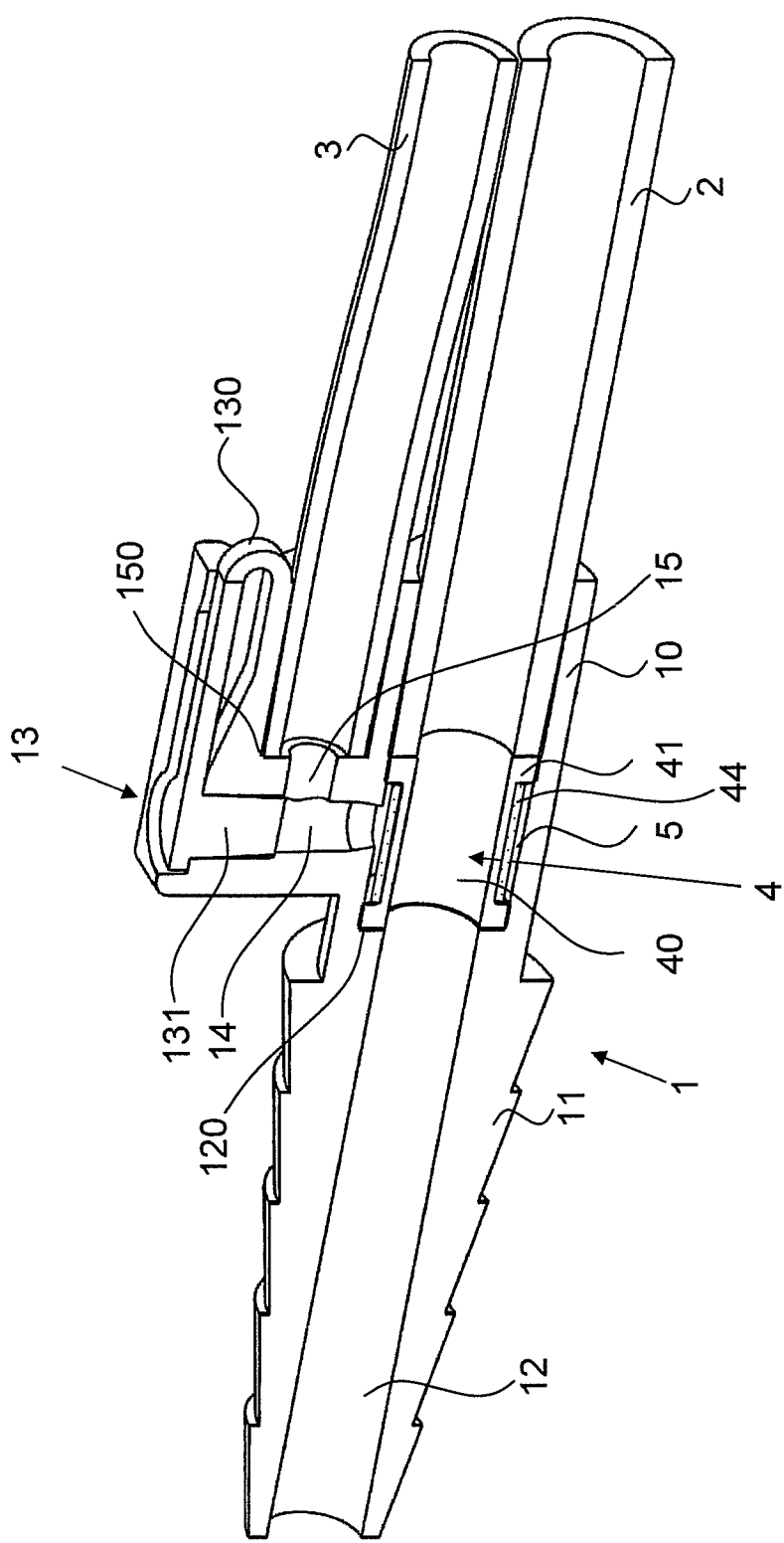
FIG. 12 shows a longitudinal section through a coupling part according to the invention, with tubes arranged therein, in a third embodiment.

FIG. 12 shows a third embodiment of the coupling part 1 according to the invention, with tubes 2 and 3 arranged therein. Here too, identical parts are provided with identical reference signs and are not repeated in detail here. The coupling part has the main body 10 and the patient-side drainage attachment 11 arranged thereon. Main body 10 and drainage attachment 11 are again preferably formed together in one piece.

In this example, both orifices for patient-side ends of the drainage tube 2 and of the service tube 3 are formed in the main body 10. The diameter of the service tube 3 is again preferably smaller than the diameter of the drainage tube 2. Both tubes 2, 3 are preferably designed with a single lumen and they extend separately from each other at least in the area of the coupling part 1.

At the opposite end, the main body 10 merges into the patient-side drainage attachment 11. The drainage attachment 11 is again preferably conical and stepped. The drainage attachment 11 is in axial alignment with the pump-side orifice for the drainage tube 2. The drainage channel 12, which is preferably rectilinear along its entire length, extends between this orifice and the patient-side free end of the drainage attachment 11.

The diameter of the pump-side orifice for the service tube 3 is accordingly smaller than that of the pump-side orifice for the drainage tube 2. The second orifice is axially offset with respect to the first orifice in the main body 10, and leads into the rectilinear service channel 15 extending parallel to the drainage channel 12. The service channel 15 in the interior of the main body 10 preferably narrows and thus forms a step 150. This step 150 serves as an abutment for the patient-side end of the service tube 3.

The service channel 15 ends in the main body 10 and opens into a connection channel 14, which preferably extends perpendicular to the service channel 15. The connection channel 14 has the same diameter as or a smaller diameter than the service channel 15. The connection channel 14 ends on the one hand in the drainage channel 12, preferably opening into the drainage channel 12 perpendicular to the longitudinal direction of the drainage channel 12. The other end of the connection channel 14 forms an opening to the outside, which preferably extends perpendicular to the pump-side orifices of the drainage channel 12 and of the service channel 15. It is also possible that the connection channel has an angle, is designed in a curved shape and/or opens at a different angle into the drainage channel 12 or the service channel 15.

The outwardly directed opening of the connection channel 14 is closed by a closure lid 13, which is shown in the closed state in FIG. 12. The connection channel 14 is preferably produced in one piece with the rest of the coupling part 1. The connection channel 14 has a closure band 130 which is formed integrally with a first end on the main body 10. At a second end, a stopper 131 is formed integrally on the closure band 130 and can be plugged into the outwardly directed opening of the connection channel 14, and can thus close the connection channel 14 in an airtight and liquid-tight manner.

Instead of a membrane, a filter 4, which is air-permeable but liquid-tight, i.e. not permeable to liquids, is formed in the coupling part 1. The filter 4 separates the service channel 15 from the drainage channel 12. Fluid, which is aspirated from a cavity in the patient by a suction pump connected to the drainage tube 2, flows unimpeded through the drainage channel 12 without passing through the filter. However, the same fluid cannot reach directly into the service channel 15 and instead has to flow through the filter in this case. This prevents aspirated liquid, tissue particles or other solids from passing into the service channel 15 and the service tube 3 and blocking them.

The filter 4 is preferably arranged in the drainage channel 12, in which it closes the orifice of the connection channel 14 into the drainage channel 12 or is arranged in this area. In this example, there is a distance between filter 4 and orifice. The resulting free space 5 is preferably annular and extends radially around the entire longitudinal center axis L of the drainage channel 12. This distance facilitates the pressure measurement in the drainage channel 12, with the pressure being measured in this area.

The filter 4 is preferably designed as an insert element, which can be secured in the main body 10 or in the drainage attachment 11. The filter 4 preferably has a hollow cylindrical shape or a tubular shape and, in the assembled state, extends coaxially with respect to the drainage channel 12. The filter 4 has a material that performs the filter function, in this case a filter element 44 extending along the jacket of the hollow cylinder shape. In this way, fluid aspirated from the cavity in the patient flows through the drainage channel 12 without passing through the filter element 44. However, the annular free space 5, which is connected to the service channel 15, is located on the other side of the filter element 44.

At the transition from the main body 10 to the patient-side drainage attachment 11, the drainage channel 12 has a step 120. The drainage channel 12 in the drainage attachment part 11 therefore has a smaller diameter than the section of the drainage channel 12 in the main body 10. The step 120 serves as an abutment for the filter 4. The remaining section of the drainage channel 12, that is to say the pump-side section, preferably has an internal diameter at least the same size as the external diameter of the filter 4. In this way, the filter 4 can be easily pushed or pressed from the pump-side orifice through the drainage channel 12 and as far as the abutment 120. The pump-side end of the filter 4 then preferably serves as an abutment for the drainage tube 2. There is preferably a compression packing between the filter 4 and the inner wall of the rest of the coupling part 1, such that no secretion liquid can pass into the service channel 15 and, therefore, a pressure measurement can be carried out unaffected in this channel.

Figure 13:
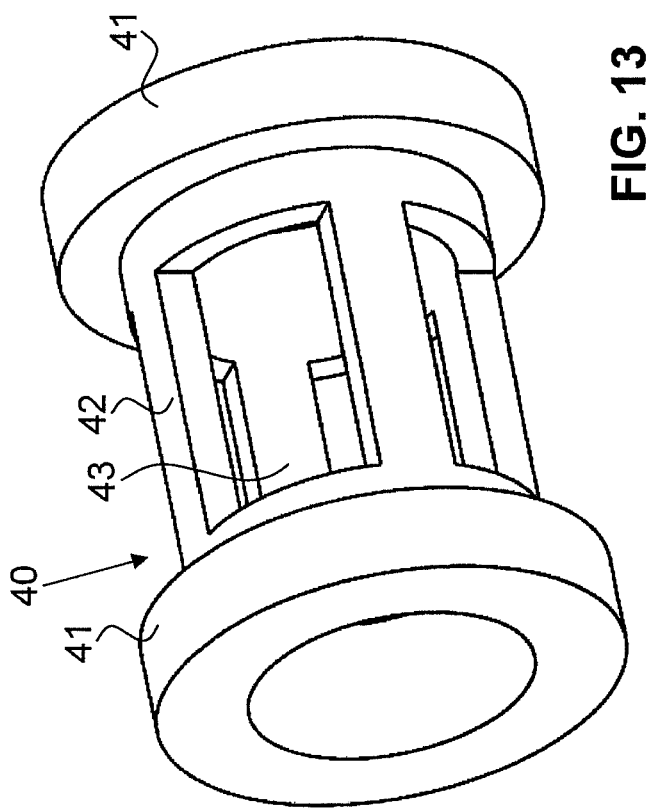
FIG. 13 shows a perspective view of a support body, according to the invention, of a filter according to the third embodiment.

The filter 4 can be composed entirely of the filter element 44, which is designed to be self-supporting. However, as is shown here, the filter 4 preferably has a dimensionally stable support body 40 on which the filter element 44 is arranged. A preferred embodiment of the support body 40 is shown in FIG. 13. The support body 40 is dumbbell-shaped and has two mutually opposite end flanges 41 with widened diameter. The two end flanges 41 are connected to each other via longitudinal webs 42, and continuous windows 43 are formed between the longitudinal webs 42. Through these windows 43, air can pass into the connecting channel 14 and to the service channel 15. The support body 40 is preferably made of plastic or metal and is preferably designed in one piece.

Figure 14:
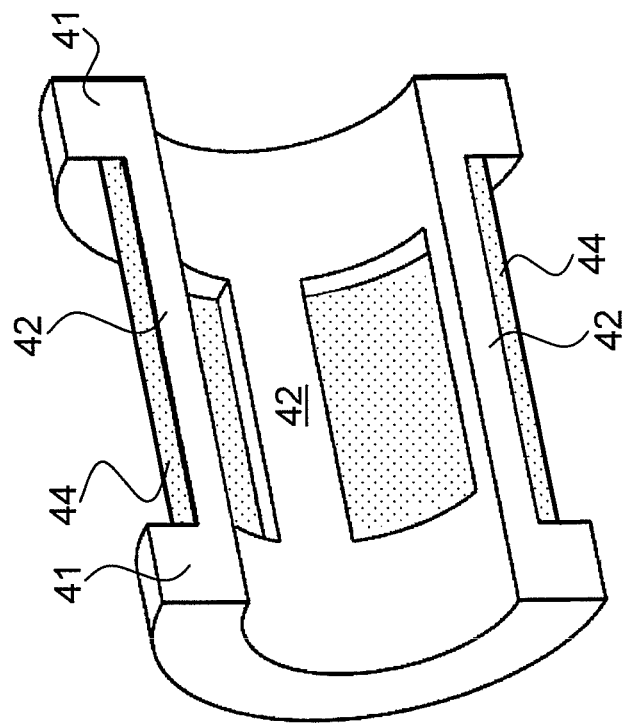
FIG. 14 shows a longitudinal section through the support body according to FIG. 13 in a perspective view, with a filter element arranged on the support body.

FIG. 14 shows a possible variant of the arrangement of the filter element 44, which performs the filter function. The filter element 44 is wound between the two end flanges 41 around the longitudinal webs 42, such that it closes the windows 43. The filter element 44 thus forms, together with the end flanges 41, the outer periphery of the filter insert 4. In the assembled state, the filter element 44 preferably has a smaller external diameter than the support body 40. In the unwound state, the filter element 44 preferably has a rectangular basic shape.

The filter element 44 is preferably made of a material that is hydrophobic and in particular also oleophobic. The material is preferably relatively flexible, such that it can be easily wound around the support body 40.

Alternatively or in addition, the filter element 44 can also be arranged on the inner face of the support body 40. In this way, the filter element has increased stability.

The filter element 44 can be injected onto, adhesively bonded, welded or otherwise connected to the support body 40.

Instead of webs and windows, a large number of slits or differently shaped openings can be provided in an inherently closed main body of the support body. The slits or openings are then covered by the filter element.

The filter, i.e. the support body 40 and/or the self-supporting filter element 44, can also have a cross-sectional shape different from a round cross section. For example, the filter can be oval or polygonal, in particular square or triangular.

Figure 15:
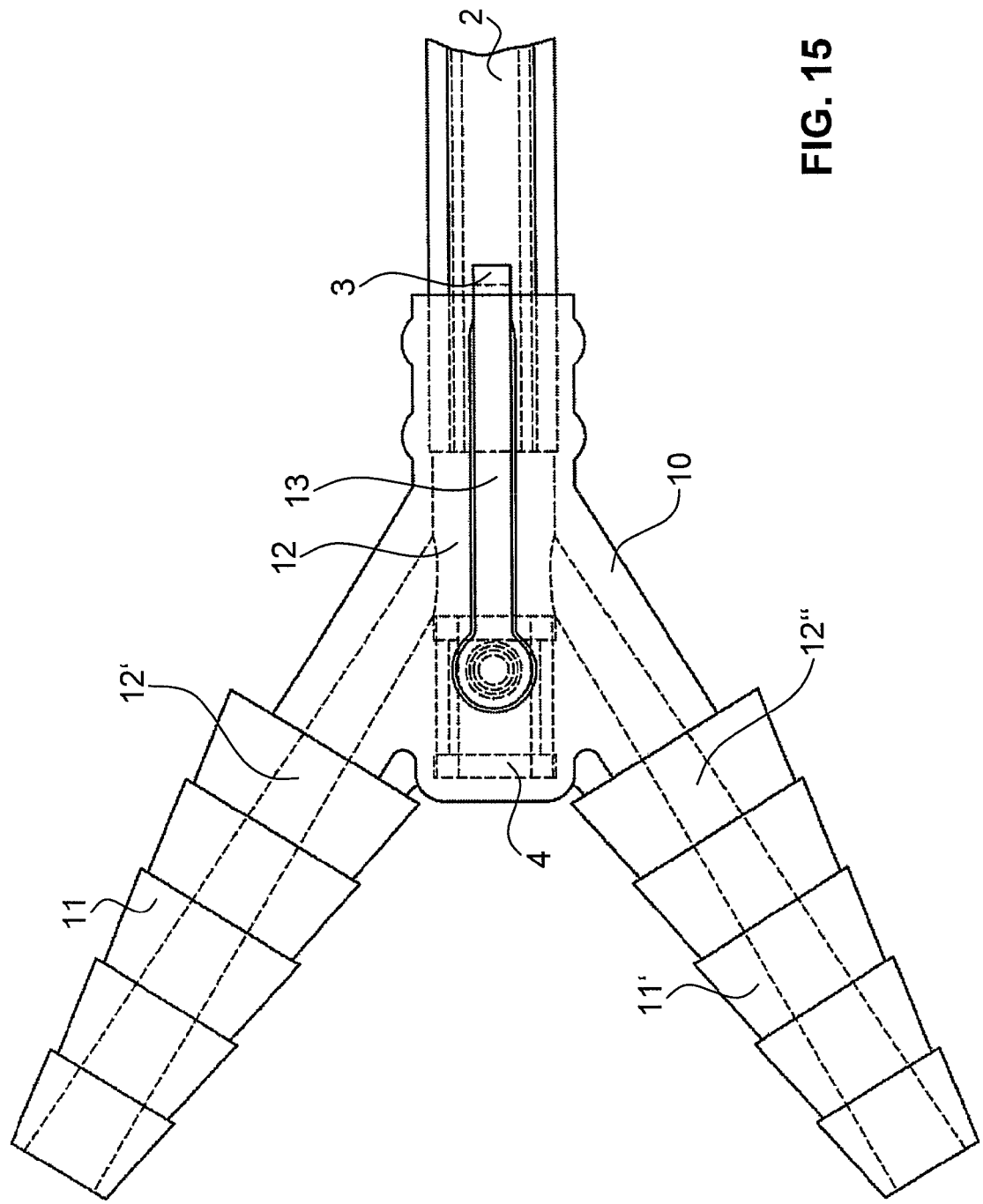
FIG. 15 shows a view of a coupling part according to the invention in a fourth embodiment from above.
Figure 16:
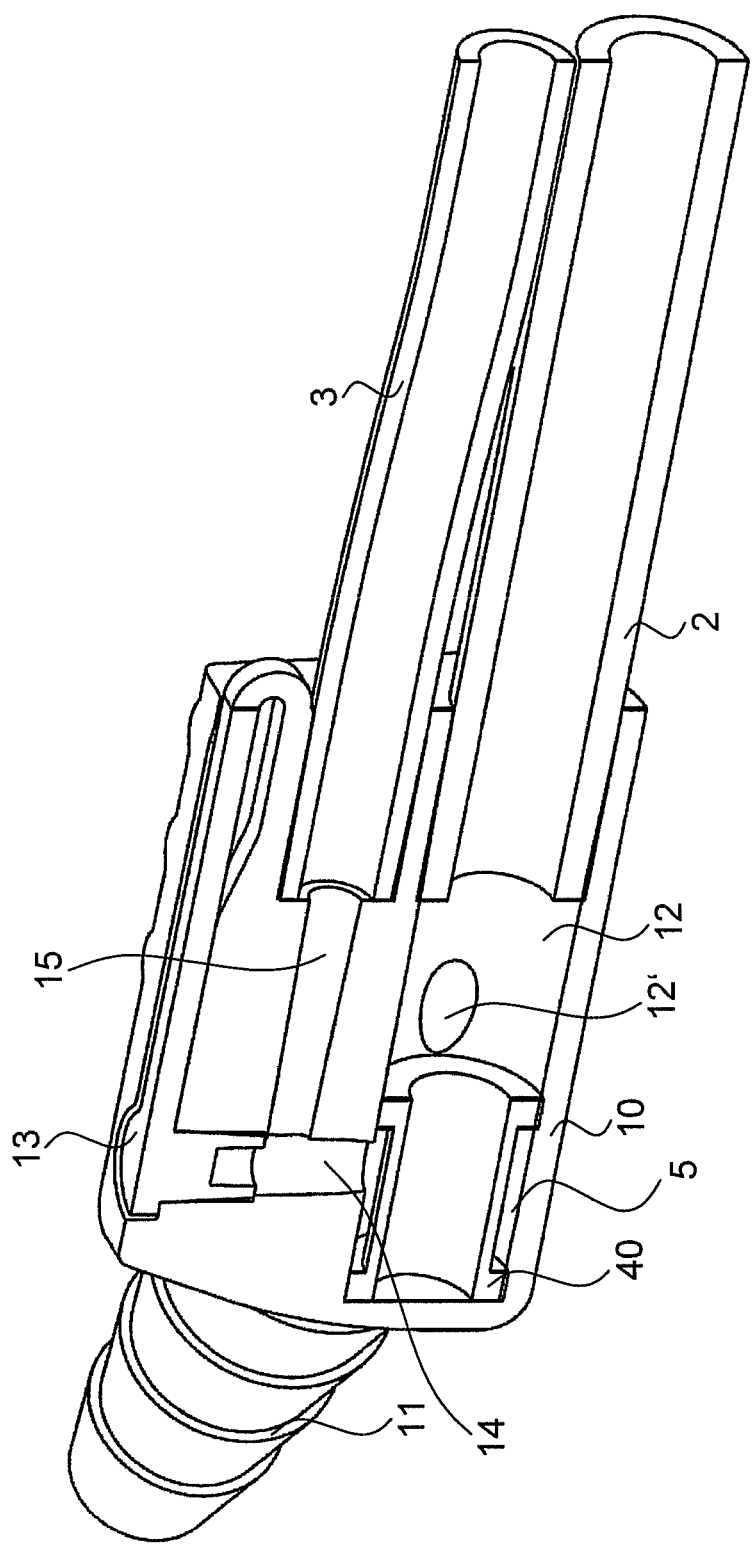
FIG. 16 shows a longitudinal section through the coupling part according to FIG. 15 in a perspective view.
Figure 17:
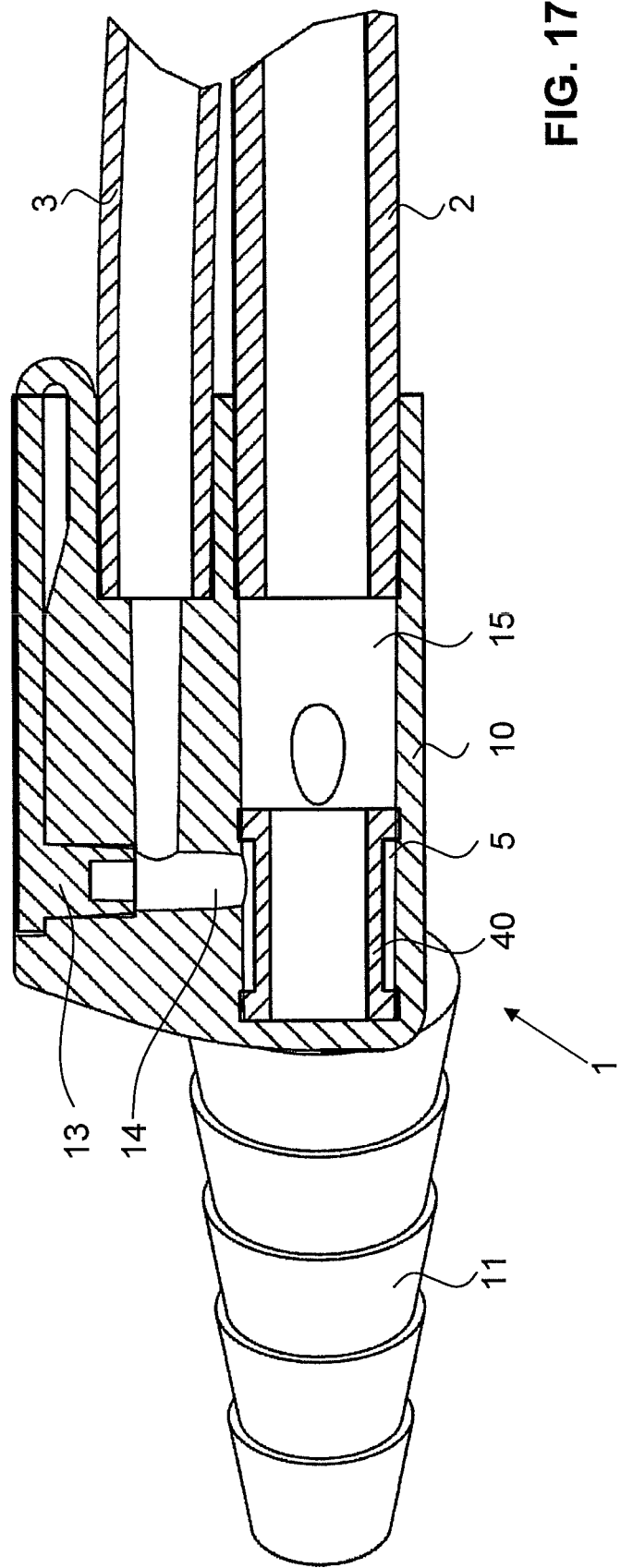
FIG. 17 shows a longitudinal section through the coupling part according to FIG. 15.

The same filter insert 4 can also be used in another embodiment of the coupling part 1 according to the invention. This is shown in FIGS. 15 to 17. The basic structure corresponds to the illustrative embodiment already described, such that identical parts are provided with the same reference numbers. A main body 10 is also present here. However, the main body has three ends and is therefore Y-shaped. A first, pump-side end once again has two mutually spaced apart orifices for a drainage tube 2 and a service tube 3 (see FIGS. 16 and 17). However, there are two patient-side ends, which are preferably designed identically. On each end there is a patient-side drainage attachment 11, 11'. Both are preferably of the same length and are designed with the same cross section as the drainage channel 12', 12". The pump-side single-lumen drainage channel 12 thus branches inside the main body 10 into two preferably identical drainage channel branches 12', 12". In the direction of aspiration, the bifurcation preferably takes place upstream of the orifice of the service channel 14 into the drainage channel 12. That is to say, the drainage channel 12 in the main body 10 has a branch that continues past the bifurcation of the drainage channel branches 12', 12" and preferably forms the rectilinear patient-side continuation of the drainage channel 12. The continuation is preferably long enough to receive the filter 4, without the filter 4 protruding into the area of the bifurcation to the drainage channel branches 12', 12". In this way, aspirated fluid does not flow through the filter 4. This arrangement avoids premature saturation of the filter material.

Here too, the filter 4 can again be pushed or pressed into its position of use via the pump-side orifice of the drainage channel 12. However, the filter can also be pushed into the main body 10 from a patient-side end thereof lying between the two drainage attachments 11, 11' (this variant is not illustrated here).

Instead of the abovementioned filter insert, other filters can also be used in both of the embodiments described with reference to FIGS. 12 to 17. Moreover, other forms of membranes described with reference to the above FIGS. 1 to 11 or other types of nonreturn valves can also be used. Moreover, the described filter and the described membrane can also be used in other embodiments.

The coupling part according to the invention, with its device for separating the service channel from the drainage channel, permits a reliable measurement of pressure.

The invention claimed is:

1. A coupling part of a drainage tube unit for aspirating body fluids by means of a suction pump, comprising:
   a patient-side drainage attachment, a pump-side drainage orifice for connection to a drainage tube, and a drainage channel connecting the drainage attachment and the drainage orifice to each other;
   a pump-side first service orifice for connection to a service tube, a second service orifice ending in the interior of the coupling part, and a service channel connecting these first and second service orifices; and a device which separates the service channel from the drainage channel, wherein the device permits delivery of fluid from the service channel into the drainage channel and prevents delivery of particles and liquid from the drainage channel into the service channel;

wherein the device is arranged in the coupling part at a location that allows a flow through the drainage channel from the drainage attachment to the drainage orifice without passage through the device;

wherein the pump-side drainage orifice and the pump-side service orifice extend parallel to each other and wherein the device is a membrane, the membrane acting as a filter and/or as a nonreturn valve.

2. The coupling part as claimed in claim 1, further comprising a connection channel for connecting the second service orifice to the drainage channel, wherein the device is arranged in the area of the connection channel.

3. The coupling part as claimed in claim 1, wherein the service channel and the drainage channel extend parallel to each other.

4. A coupling part of a drainage tube unit for aspirating body fluids by means of a suction pump, comprising:

a patient-side drainage attachment, a pump-side drainage orifice for connection to a drainage tube, and a drainage channel connecting the drainage attachment and the drainage orifice to each other;

a pump-side first service orifice for connection to a service tube, a second service orifice ending in the interior of the coupling part, and a service channel connecting these first and second service orifices; and a device which separates the service channel from the drainage channel, wherein the device permits delivery of fluid from the service channel into the drainage channel and prevents delivery of particles and liquid from the drainage channel into the service channel;

wherein the device is arranged in the coupling part at a location that allows a flow through the drainage channel from the drainage attachment to the drainage orifice without passage through the device, wherein the device has a filter which is permeable to air and impermeable to liquid.

5. The coupling part as claimed in claim 1, wherein the membrane comprises a duckbill valve.

6. The coupling part as claimed in claim 1, wherein the membrane is round and has, in its peripheral area, at least one circumferential and closed sealing lip.

7. The coupling part as claimed in claim 1, further comprising a main body with a membrane seat for receiving the membrane, and a lid with which the main body in the area of the membrane seat is closed from the outside in a leaktight manner.

8. The coupling part as claimed in claim 7, wherein the service channel is arranged in the lid.

9. The coupling part as claimed in claim 1, wherein the membrane forms a membrane surface that is parallel to a longitudinal axis of the drainage channel.

10. The coupling part as claimed in claim 1, wherein the membrane is arranged asymmetrically with respect to a longitudinal center axis of the drainage channel.

11. The coupling part as claimed in claim 1, further comprising an injection and/or withdrawal opening, which connects an outer face of the coupling part to the drainage channel.

12. The coupling part as claimed in claim 1, further comprising two drainage channels and a single service channel, wherein the service channel is connected to both drainage channels, and wherein the device has a single membrane that separates both drainage channels from the service line.

13. The coupling part as claimed in claim 4, wherein the device has a tubular shape and extends coaxially with respect to the drainage channel.

14. The coupling part as claimed in claim 13, wherein the device has a support body and a filter element that performs a filter function, wherein the filter element is arranged on and/or in the support body.

15. The coupling part as claimed in claim 1, further comprising a chamber and wherein the service channel ends in the chamber and wherein the chamber merges into a connection channel, which opens out in the drainage channel.

16. The coupling part as claimed in claim 1, further comprising a connection channel and wherein the service channel ends in the connection channel, which opens out in the drainage channel.

17. The coupling part as in claim 15, wherein the connection channel is perpendicular to the service channel.

18. The coupling part as in claim 16, wherein the connection channel is perpendicular to the service channel.

19. The coupling part as claimed in claim 15, wherein the device is arranged within the chamber.

20. The coupling part as claimed in claim 4, further comprising a connection channel for connecting the second service orifice to the drainage channel, wherein the device is arranged in the area of the connection channel.

21. The coupling part as claimed in claim 4, wherein the service channel and the drainage channel extend parallel to each other.

22. The coupling part as claimed in claim 4, wherein the pump-side drainage orifice and the pump-side service orifice extend parallel to each other.

23. The coupling part as claimed in claim 4, further comprising an injection and/or withdrawal opening, which connects an outer face of the coupling part to the drainage channel.

24. The coupling part as claimed in claim 4, further comprising two drainage channels and a single service channel, wherein the service channel is connected to both drainage channels, and wherein the filter separates as a single filter both drainage channels from the service line.

25. The coupling part as claimed in claim 4, further comprising a chamber and wherein the service channel ends in the chamber and wherein the chamber merges into a connection channel, which opens out in the drainage channel.

26. The coupling part as claimed in claim 4, further comprising a connection channel and wherein the service channel ends in the connection channel, which opens out in the drainage channel.

27. The coupling part as in claim 25, wherein the connection channel is perpendicular to the service channel.

28. The coupling part as in claim 26, wherein the connection channel is perpendicular to the service channel.

29. The coupling part as claimed in claim 25, wherein the device is arranged within the chamber.

* * * * *